US012758182B2

(12) United States Patent
Eldar et al.

(10) Patent No.: US 12,758,182 B2
(45) Date of Patent: Oct. 13, 2026

(54) MEDICAL IMAGING WITH NONLINEAR WAVEFORM INVERSION (NLWI) SYSTEM USING RECURRENT NEURAL NETWORK

(71) Applicant: Yeda Research and Development Co. Ltd, Rehovot (IL)

(72) Inventors: Yonina Eldar, Rehovot (IL); Avner Shultzman, Rehovot (IL)

(73) Assignee: Yeda Research And Development Co. Ltd, Rehovot (IL)

( * ) Notice: Subject to any disclaimer, the term of this patent is extended or adjusted under 35 U.S.C. 154(b) by 0 days.

(21) Appl. No.: 18/862,562

(22) PCT Filed: May 3, 2023

(86) PCT No.: PCT/IL2023/050456

§ 371 (c)(1),
(2) Date: Nov. 4, 2024

(87) PCT Pub. No.: WO2023/218443

PCT Pub. Date: Nov. 16, 2023

(65) Prior Publication Data

US 2025/0288276 A1 Sep. 18, 2025

Related U.S. Application Data

(60) Provisional application No. 63/375,545, filed on Sep. 14, 2022, provisional application No. 63/339,473, filed on May 8, 2022.

(51) Int. Cl.

| | |
|---|---|
| ***A61B 8/00*** | (2006.01) |
| ***A61B 8/08*** | (2006.01) |
| ***G01S 15/89*** | (2006.01) |

(52) U.S. Cl.

CPC .......... *A61B 8/0858* (2013.01); *A61B 8/5207* (2013.01); *A61B 8/5292* (2013.01); *G01S 15/8977* (2013.01)

(58) Field of Classification Search

CPC ... A61B 8/0858; A61B 8/5207; A61B 8/5292; A61B 8/5223; A61B 8/085; G01S 15/8977

See application file for complete search history.

(56) References Cited

U.S. PATENT DOCUMENTS

2017/0261538 A1 9/2017 Kamilov
2018/0279965 A1* 10/2018 Pandit .................. A61B 5/0285

(Continued)

FOREIGN PATENT DOCUMENTS

WO WO-2021116800 A1 * 6/2021 ............. G01V 1/282

OTHER PUBLICATIONS

International Search Report issued in corresponding application PCT/IL2023/050456 mailed on Jul. 26, 2023.

(Continued)

*Primary Examiner* — Joel Lamprecht
*Assistant Examiner* — James F McDonald, III
(74) *Attorney, Agent, or Firm* — Heidi Brun Associates Ltd.; Heidi M. Brun

(57) ABSTRACT

A system for recovering physical properties from a non-linear medium includes a wave field modeler, a properties adjuster and a medium properties recoverer. The wave field modeler models a wave field generated by a transmitted pulse traveling in the non-linear medium and generates a predicted transducer output from the modeled wave field. The wave field modeler is a neural network having a neural network representation of a non-linear wave function of the physical properties of the wave field. The properties adjuster optimizes a loss function between the predicted transducer output and a measured transducer output and generates an improved set of the physical properties. The properties adjuster operates a backpropagator using the neural network representation and activates the wave field modeler with the (Continued)

improved set of the physical properties. The medium properties recoverer outputs a current improved set of the physical properties once the properties adjuster finishes operation.

14 Claims, 14 Drawing Sheets

(56) References Cited

U.S. PATENT DOCUMENTS

| | | | | |
|---|---|---|---|---|
| 2020/0271577 | A1 | 8/2020 | Mansour | |
| 2020/0311878 | A1* | 10/2020 | Matsuura | G06T 5/70 |
| 2020/0395117 | A1* | 12/2020 | Schnorr | G16H 50/20 |
| 2021/0015456 | A1* | 1/2021 | Chiang | A61B 8/0883 |
| 2021/0169336 | A1* | 6/2021 | Sanchez | A61B 5/7264 |

OTHER PUBLICATIONS

Felix Lucka et al., "High Resolution 3D Ultrasonic Breast Imaging by Time-Domain Full Waveform Inversion", Arxiv.org, Cornell University Library, Mar. 10, 2021.

Shultzman Avner et al., "Nonlinear Waveform Inversion for Quantitative Ultrasound", IEEE Transactions on Computational Imaging, vol. 8, Sep. 21, 2022, pp. 893-904.

* cited by examiner

MEDICAL IMAGING WITH NONLINEAR WAVEFORM INVERSION (NLWI) SYSTEM USING RECURRENT NEURAL NETWORK

CROSS REFERENCE TO RELATED APPLICATIONS

This application is a National Phase Application of International Application No. PCT/IL2023/050456 having an international filing date of May 3, 2023 which claims priority from U.S. provisional patent applications 63/339,473, filed May 8, 2022, and U.S. Pat. No. 63,375,545, filed September 2022, all of which are incorporated herein by reference.

FIELD OF THE INVENTION

The present invention relates to nonlinear waveform inversion in general and to its application to ultrasound in particular.

BACKGROUND OF THE INVENTION

Due to its non-invasive and non-radiating nature, ultrasound imaging is widely used in medical applications. Reference is made to FIGS. 1A thru 1G which illustrate the structure and operation of a typical ultrasound system 10. As shown in FIG. 1A, ultrasound system 10 has a transducer 11 and a medium 16 containing tissues 17. Transducer 11 has a transducer array 12 which is made up of a number, $n_c$, of transducer elements, each containing a transmitter 15 and a receiver 13. FIG. 1A is shown at time to before operation.

In ultrasound imaging, an image is generated by ionizing or transmitting one or a series of acoustic pulses from array of transducer elements 12, as shown in FIGS. 1B, 1C and 1D. FIG. 1B shows pulse 21 exiting transducer 11 at a starting time, shown as t1. FIG. 1C shows pulse 22 exiting transducer 11 at a later time, shown as t2, and pulse 21 continuing to travel away from transducer 11. FIG. 1D shows pulse 23 exiting transducer 11 at time t3, and pulse 22 and pulse 21 continuing propagation away from transducer 11.

Transmitted pulses 21, 22 and 23 propagate through medium 16 and tissues 17, leading to a sequence of reflections and refractions, which create echoes that are then detected by the same array. FIG. 1E shows the first reflected wave 24 at time t4 (transmitted pulses 21, 22 and 23 have been omitted for clarity) travelling towards transducer 11. FIG. 1F shows a second reflected wave 25, following wave 24 at time t5. FIG. 1G shows wave 24 reaching transceiver 11 at time t6. At time t6, transceiver 11 acquires the ultrasound signal, after which, beamforming algorithms are used to align the signals from different transducer elements properly, and the data acquired from multiple transmission schemes are combined to generate an ultrasound image of medium 16 and tissues 17.

Typical Brightness-mode (B-mode) images are generated by applying corresponding time delays to the acquired signal and averaging over the channels with tailored weights. Nevertheless, B-mode images do not necessarily provide sufficient contrast for certain anatomical structures and have poor physical interpretation.

Imaging of physical properties of the material, such as speed-of-sound (SoS), density, acoustic attenuation, and elasticity, is known to have valuable differentiation capabilities and to improve medical diagnosis. For example, SoS maps can discern between benign and malignant breast tumors, identify muscle loss and fatty muscular degeneration (sarcopenia) in seniors, and differentiate between healthy and diseased tissues, such as in human and animal livers, affected by nonalcoholic fatty liver disease (NAFLD). Acoustic attenuation maps can improve the diagnosis of non-healthy tissues. Finally, the tissue density can indicate a risk for breast cancer, and can quantify the level of fat and steatosis in the liver, which is critical to monitor NAFLD and nonalcoholic steatohepatitis (NASH).

Inverse ultrasound algorithms seek to reconstruct the properties of a medium based on the acquired ultrasound signal. A standard method to solve the inverse ultrasound problem is the full waveform inversion (FWI) algorithm, a computational technique initially developed in geophysics. It relies on a physical wave propagation model and therefore explains a broader range of phenomena compared to B-mode images. To reconstruct the properties, the algorithm utilizes a computationally heavy, iterative gradient-based approach.

Other inverse ultrasound methods use a differential path matrix to estimate the speed-of-sound of the medium. The differential path matrix links the SoS distribution to the obtained time delays at the transducer. However, the differential path matrix only estimates the medium's SoS, since it depends on geometric considerations rather than on the wave propagation model. Alternative solutions to the inverse ultrasound problem use machine learning approaches, such as deep neural networks. Such approaches require a significant amount of known medical data with known SoS maps in order to train the neural networks, and the obtained models have poor interpretability.

SUMMARY OF THE PRESENT INVENTION

There is therefore provided, in accordance with a preferred embodiment of the present invention, a system for recovering physical properties from a non-linear medium. The system includes a wave field modeler, a properties adjuster and a medium properties recoverer. The wave field modeler models a wave field generated by at least one transmitted pulse as it travels in the non-linear medium and generates a predicted transducer output from the modeled wave field. The wave field modeler is implemented as a neural network having a neural network representation of a non-linear wave function of a set of physical properties of the wave field. The properties adjuster optimizes a loss function between the predicted transducer output and a measured transducer output and generates an improved set of the physical properties. The properties adjuster operates a backpropagator using the neural network representation of the wave function and activates the wave field modeler with the improved set of the physical properties. The medium properties recoverer outputs a current improved set of the physical properties once the properties adjuster finishes operation. The current improved set of the physical properties are the recovered physical properties of the non-linear medium.

Moreover, in accordance with a preferred embodiment of the present invention, the medium is a two or three dimensional body tissue.

Furthermore, in accordance with a preferred embodiment of the present invention, the wave field is one of: an acoustic, an electromagnetic, an elastic, a photo-acoustic, and an acousto-optic wave.

Further, in accordance with a preferred embodiment of the present invention, the transmitted pulse(s) is one of: a plane wave, a focused beam, and a diverging wave.

Still further, in accordance with a preferred embodiment of the present invention, the neural network of the wave field modeler includes a non-linear function receiving the improved set of the physical parameters as input and to which two previous wave samples and a pulse sample are provided.

Moreover, in accordance with a preferred embodiment of the present invention, the wave field modeler also includes a restriction operator to restrict an output of the neural network to one of a linear array of elements, a convex array of elements, an elliptic array of elements, and an endo-cavitary array of elements.

Further, in accordance with a preferred embodiment of the present invention, the properties adjuster includes a plurality of error calculators, a loss accumulator and a non-linear gradient calculator. The plurality of error calculators each generate an error vector between the predicted transducer output and the measured transducer output for an associated wave field sample. The loss accumulator accumulates the error vectors, and the non-linear gradient calculator, which is implemented by the backpropagator, exploits the non-linear wave function to backpropagate gradients through the neural network, thereby to return gradients of the wave field with respect to the set of physical properties.

Still further, in accordance with a preferred embodiment of the present invention, the neural network is a recurrent neural network or a deep neural network whose layers express the time-dependence of the non-linear wave function.

There is also provided, in accordance with a preferred embodiment of the present invention, a method for recovering physical properties from a non-linear medium. The method includes modeling a wave field generated by at least one transmitted pulse as it travels in the non-linear medium, the modeling using a neural network having a neural network representation of a non-linear wave function of a set of physical properties of the wave field, generating a predicted transducer output from the modeled wave field, optimizing a loss function between the predicted transducer output and a measured transducer output to generate an improved set of the physical properties, the generating using backpropagation with the neural network representation of the wave function, activating the modeling with the improved set of the physical properties, and providing a current improved set of the physical properties once the optimizing finishes operation, wherein the current improved set of the physical properties are the recovered physical properties of the non-linear medium.

Further, in accordance with a preferred embodiment of the present invention, the modeling also includes restricting an output of the neural network to one of a linear array of elements, a convex array of elements, an elliptic array of elements, and an endo-cavitary array of elements.

Still further, in accordance with a preferred embodiment of the present invention, the optimizing includes generating an error vector between the predicted transducer output and the measured transducer output for associated wave field samples, accumulating the error vectors, and exploiting the non-linear wave function to backpropagate gradients through the neural network, thereby to return gradients of the wave field with respect to the set of physical properties.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1A:
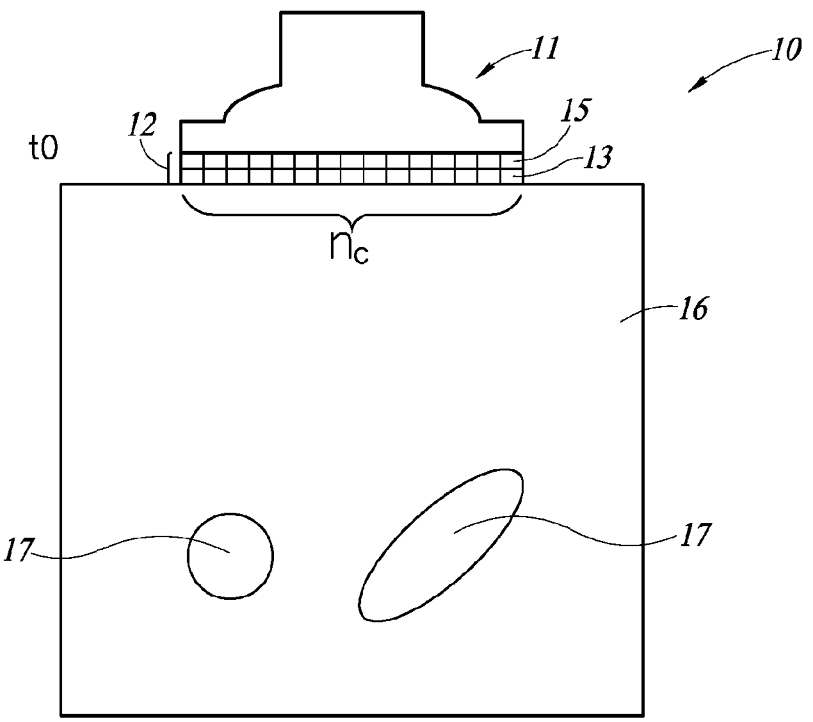
FIG. 1A (PRIOR ART)
FIGS. 1A, 1B, 1C, 1D, 1E, 1F and 1G are schematic illustrations of the operation of a prior art ultrasound imaging system.
Figure 1B:
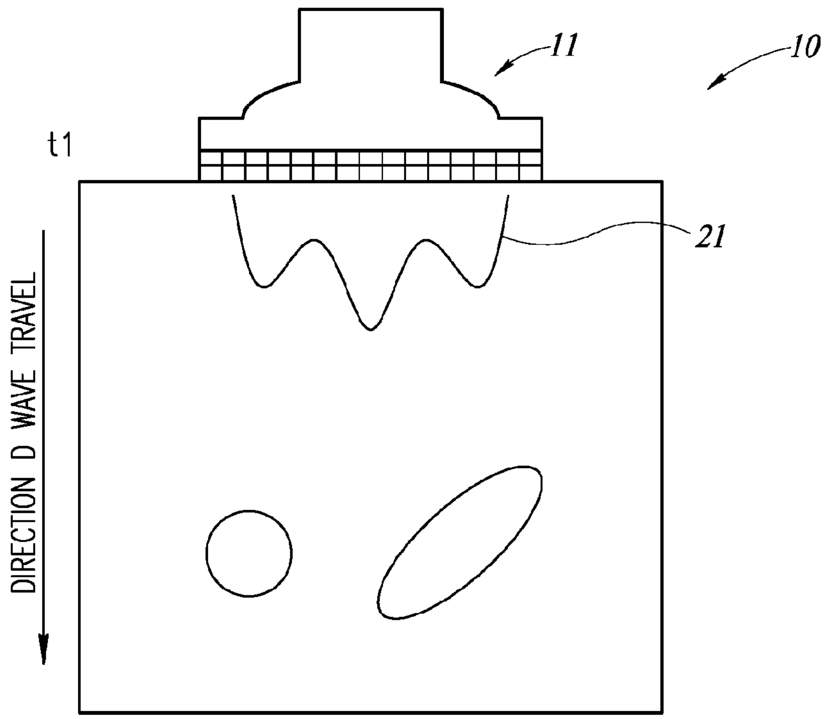
FIG. 1B (PRIOR ART)
Figure 1C:
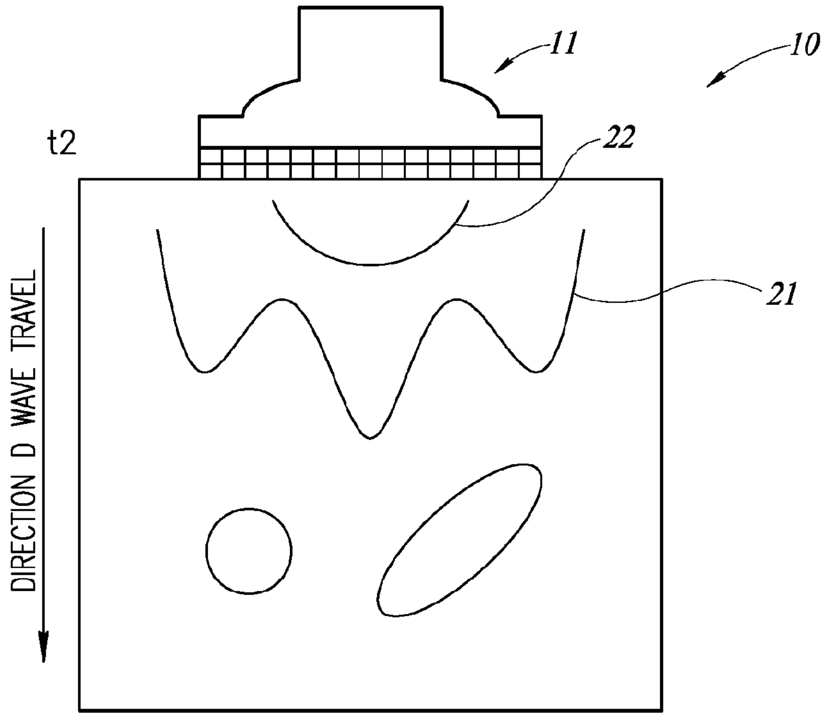
FIG. 1C (PRIOR ART)

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicant has realized that inverse acoustic algorithms work well with linear media, but are inaccurate for ultrasound medical imaging, which is usually non-linear. Moreover, the full waveform inversion (FWI) algorithms described hereinabove are computationally-heavy, making them not useful for most applications.

Applicant has realized that neural network platforms have been developed which make computationally-complicated calculations simpler to visualize and calculate and that it is possible to use a neural network, not to learn the set of parameters, but rather to express the wave equation. Applicant has realized that the neural network structure, used in deep-learning systems, may be used to express a non-linear, time-based equation, such as the wave propagation equation of the FWI. In particular, a recurrent neural network (RNN) structure can be used to express the time-based equation. Alternatively, deep neural networks, where the layers express the time-dependence of the equation, can be also used.

Moreover, Applicant has realized that such neural network systems also include differential calculations as part of their 'backpropagation' system for updating the neural network during training of the network (i.e. for learning the parameters of the neural network) and that different neural networks use different optimization algorithms in their backpropagations. Applicant has realized that the backpropagation system of a neural network system may provide a very efficient implementation for the differential calculations forming part of the iterative gradient calculation of the non-linear waveform inversion.

Thus, Applicant has realized that neural network platforms may be utilized to solve inverse nonlinear physical problems rather than to provide output given an unknown input as is the standard use of neural networks. Accordingly, a nonlinear waveform inversion system implemented on a neural network platform may be used to recover a medium's properties.

Figure 2:
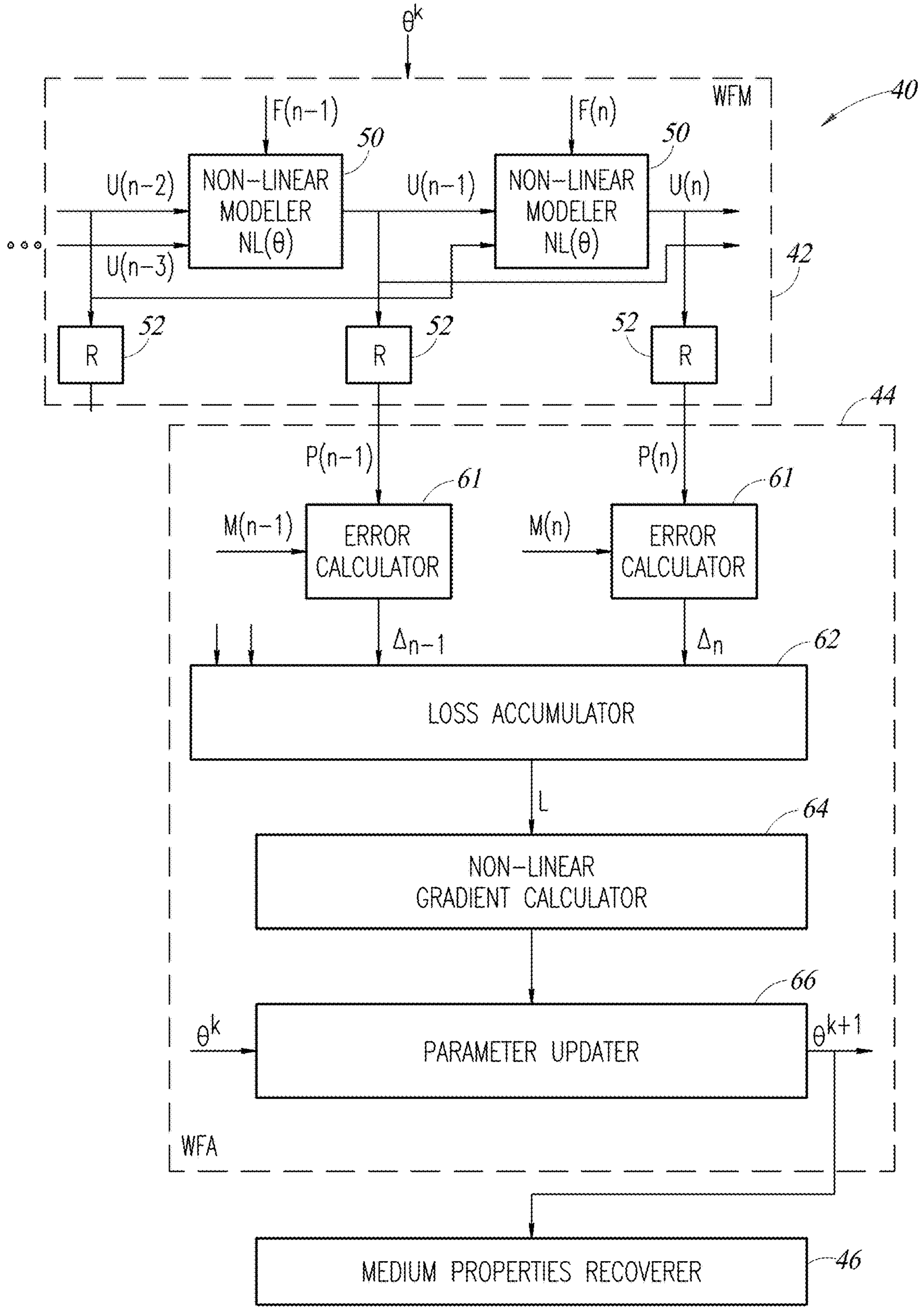
FIG. 2 is a schematic illustration of a nonlinear waveform inversion system (NLWIS), constructed and operative in accordance with a preferred embodiment of the present invention.

Reference is now made to FIG. 2 which is a schematic illustration of a nonlinear waveform inversion system (NLWIS) 40. System 40 comprises a wave field modeler (WFM) 42, a properties adjuster (PA) 44 and a medium properties recoverer (MPR) 46. System 40 may recover and output a visual representation of a physical medium through which flows a wave, such as an ultrasound wave. In ultrasound implementations, the physical medium may be a portion of the human body, such as the abdomen. The physical medium may have multiple properties θ which may affect the flow of the wave, where the elements of θ may be multiple properties, each of which may be two or three dimensional. For example, the elements of θ may be a discrete speed of sound C, a density Q, an attenuation D, and a nonlinearity B, throughout the physical medium, as will be explained in more detail hereinbelow.

Figure 1D:
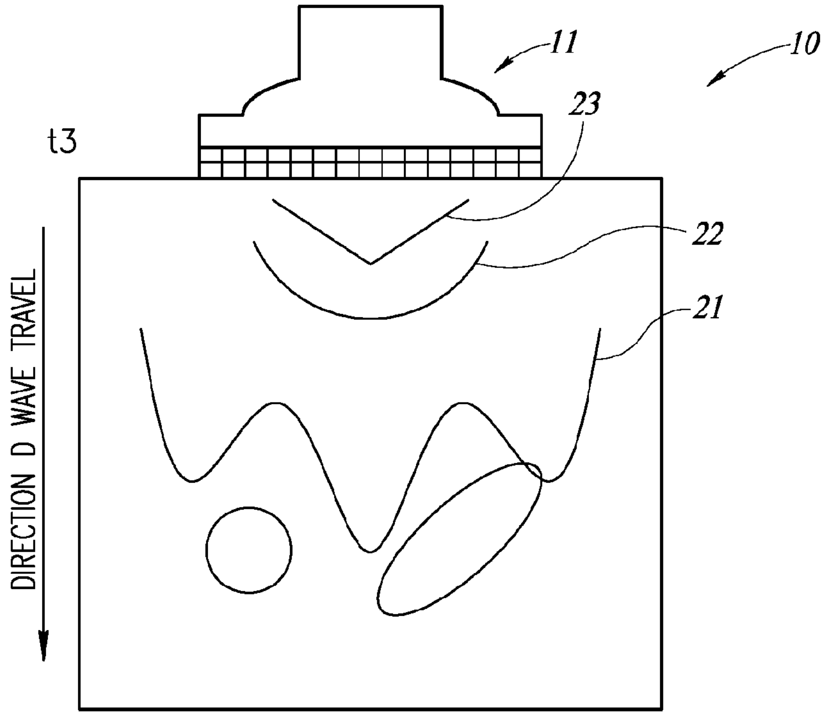
FIG. 1D (PRIOR ART)
Figure 1E:
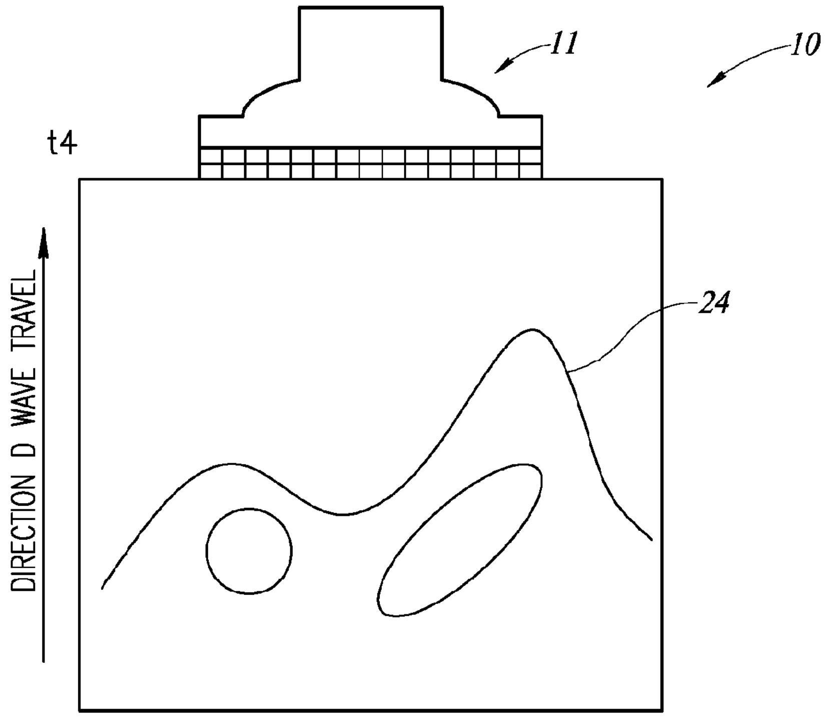
FIG. 1E (PRIOR ART)
Figure 1F:
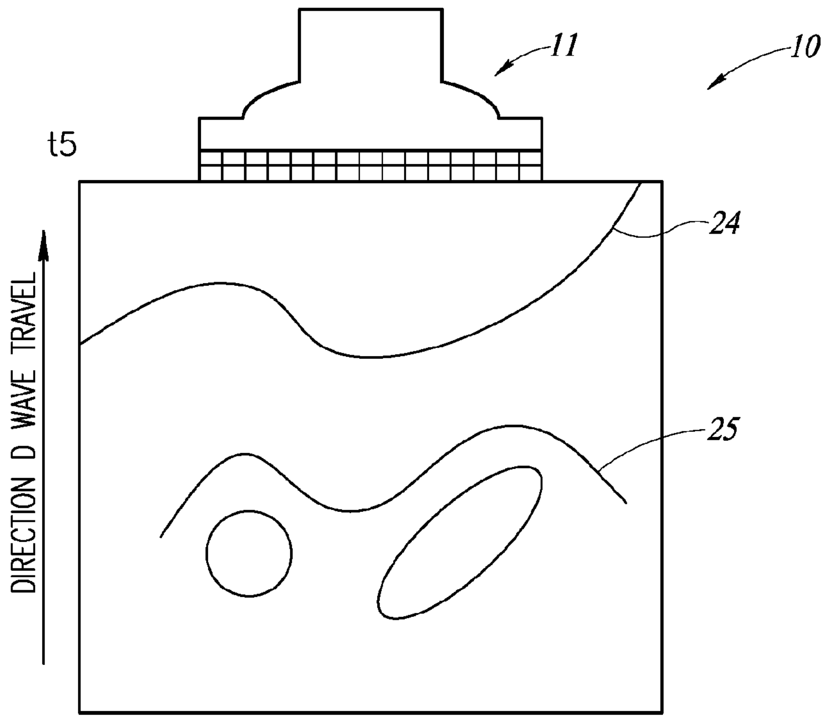
FIG. 1F (PRIOR ART)
Figure 1G:
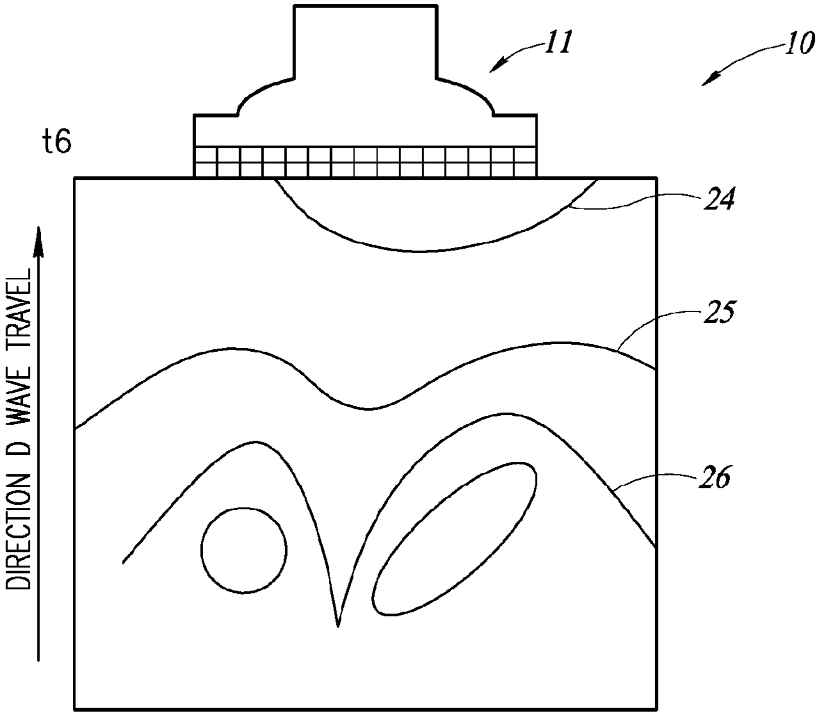
FIG. 1G (PRIOR ART)

Wave field modeler (WFM) 42 may calculate a wave field U produced in response to multiple transmitted pulses F, such as pulses 21, 22 and 23 of FIG. 1D, as they propagate through medium 16 and tissues 17. Wave field modeler 42 may use calculated wave field U to calculate detected waves P, such as reflected waves 24 and 25 of FIG. 1F when detected by receivers 13. Since wave field U may depend on the multiple properties θ and since properties θ are the unknown variables to be found, wave field modeler 42 may utilize a property estimate $\theta^k$ of properties θ and may repeat the calculation of wave field U after properties adjuster 44 may update property estimate $\theta^k$ to property estimate $\theta^{k+1}$.

Medium properties recoverer 46 may retrieve properties θ once properties adjuster 44 may indicate that estimate $\theta^{k+1}$ may have converged or after a pre-defined, maximum number of iterations k.

Figure 3A:
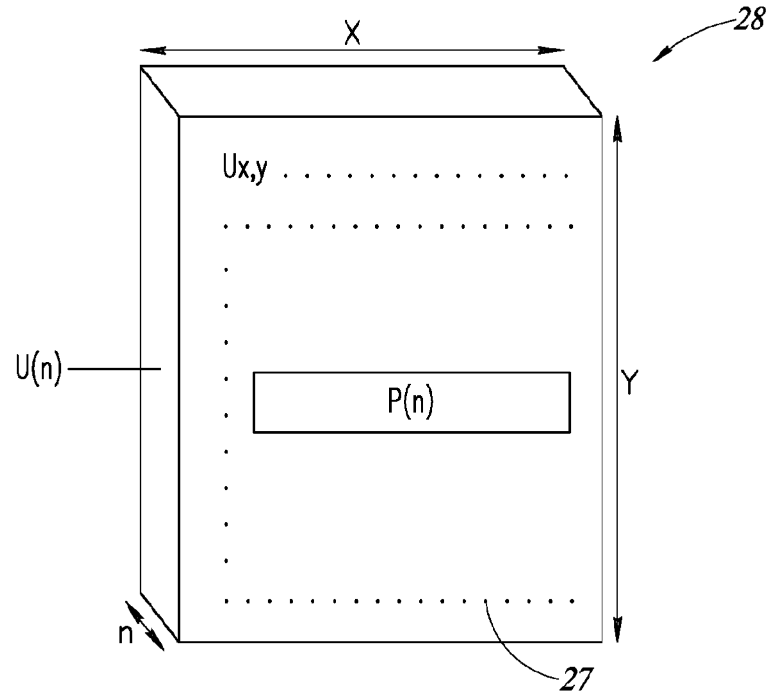
FIG. 3A is a schematic representation of a wave sample 28 at time stamp n, produced by the NLWIS of FIG. 2.
Figure 3B:
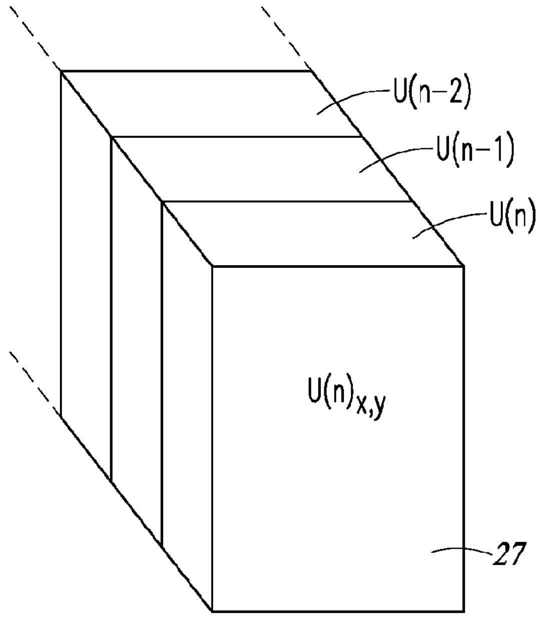
FIG. 3B is a schematic representation of multiple wave samples U(n), U(n−1)

Since system 40 is implemented on a neural network platform, system 40 uses discrete wave samples U(n) and discrete transmitted pulse samples F(n), at each time stamp n, shown in FIGS. 3A and 3B to which reference is now made. FIG. 3A is a schematic representation of a wave sample 28 at time stamp n. Wave sample 28 comprises a 2-dimensional grid 27, which contains x*y pressure values $U_{x,y}$. For example, grid 27 may be a 4000×4000 grid and wave field U may comprise N grids 27, one per time stamp n, where, in this example, N may also be 4000. Similarly, each transmitted pulse sample F(n), produced by linear transmitter 15, may have a linear grid, for example, of 128 transmitted pulses $F_x$, at each time stamp n. FIG. 3B shows multiple wave samples U(n), U(n−1), etc., where each wave sample U(n) is 2-dimensional.

Wave field modeler 42 may calculate wave field $U^k$ for each iteration k using a non-linear model NL(θ) derived from the lossy Westervelt equation, described in the article by G. Yao, et al. ("An effective absorbing layer for the boundary condition in acoustic seismic wave simulation", Journal of Geophysics and Engineering, vol. 15, no. 2, pp. 495-511, 2018) and in the book by M. F. Hamilton and D. T. Blackstock, ("Nonlinear acoustics," Academic Press., p. 55, 1998). However, the lossy Westervelt equation is a continuous equation. In accordance with a preferred embodiment of the present invention, the non-linear acoustic model implemented by wave field modeler 42 may be a discrete version thereof, as provided in equation 1:

$$U[n] = \frac{G_2}{G_1} \odot U[n-1] + \frac{G_3}{G_1} \odot U[n-2] + \frac{G_4}{G_1} \odot (U[n-1] - U[n-2])^2 + \frac{C^2 \odot Q}{G_1} \odot \left(\nabla_D * \left(\left(\frac{1}{Q}\right)\right) \cdot \nabla_D * U[n-1]\right) + \frac{C^2 \odot Q}{G_1} \odot \nabla_D^2 * U[n-1] + \frac{1}{G_1} F[n] \tag{1}$$

Where $\nabla_D$ is the discrete gradient filter, $$\nabla_D^2$$

is the discrete Laplacian filter, $1 \in \mathbb{R}^{n_x x\, n_z}$ is a matrix of ones, and $G_1$, $G_2$, $G_3$ and $G_4$ are variables built from the 2-dimensional properties C, Q, D and B, as defined in equation 2:

$$G_1 = \frac{1}{\Delta_t^2}\left(1 + 2\frac{B \odot U[n-1]}{C^2 \odot Q}\right) \tag{2}$$

$$G_2 = 2G_1 - D^2 + \frac{2}{\Delta_t} D$$

$$G_3 = -G_1 + \frac{2}{\Delta_t} D$$

$$G_4 = \frac{2}{\Delta_t^2} \frac{B}{C^2 \odot Q}$$

where Δt is a temporal interval and U(n−1) and U(n−2) are the previous two wave samples, for the current iteration k and using the values of properties C, Q, D and B determined in iteration k−1.

It is noted that in equations 1 and 2, boldface lower-case and upper-case are used for vectors and matrices, respectively. The vectorization, convolution, transpose, and element-wise multiplication (Hadamard product) operators are written as vec(•), *, $(\bullet)^T$, and ⊙, respectively. Matrix division and exponentiation are performed element-wise.

To calculate wave field $U^k$ for iteration k, wave field modeler 42 may comprise a plurality of non-linear modelers 50 (FIG. 2), each one producing one of the samples n. Each modeler 50 may implement non-linear function NL(θ), as defined in equations 1 and 2, using the values of property estimate $\theta^k$ determined at the end of the previous iteration k−1. Each non-linear modeler 50 may receive its associated 2D pulse sample F(n) as input and 2D wave samples U(n−1) and U(n−2) from its two previous non-linear modelers 50 which generated U(n−1) and U(n−2), respectively.

To predict each reflected signal P(n) received by receivers 13 (FIG. 1A), wave field modeler 42 may comprise a plurality of restriction operators 52 which may select the portion of wave sample U(n) located at the locations where receivers 13 of transducer 11 are. An example for the portion of wave sample U(n) to be used as reflected signal P(n) is shown in FIG. 3A.

It will be appreciated that wave samples U(n−2) and U(n−1) may not be available for the first wave sample U(1). In this case, all elements of initiation wave sample U(0) may be set to zero, and the input to U(1) may be just initiation wave sample U(0) and transmitted sample pulse F(1).

Figure 4:
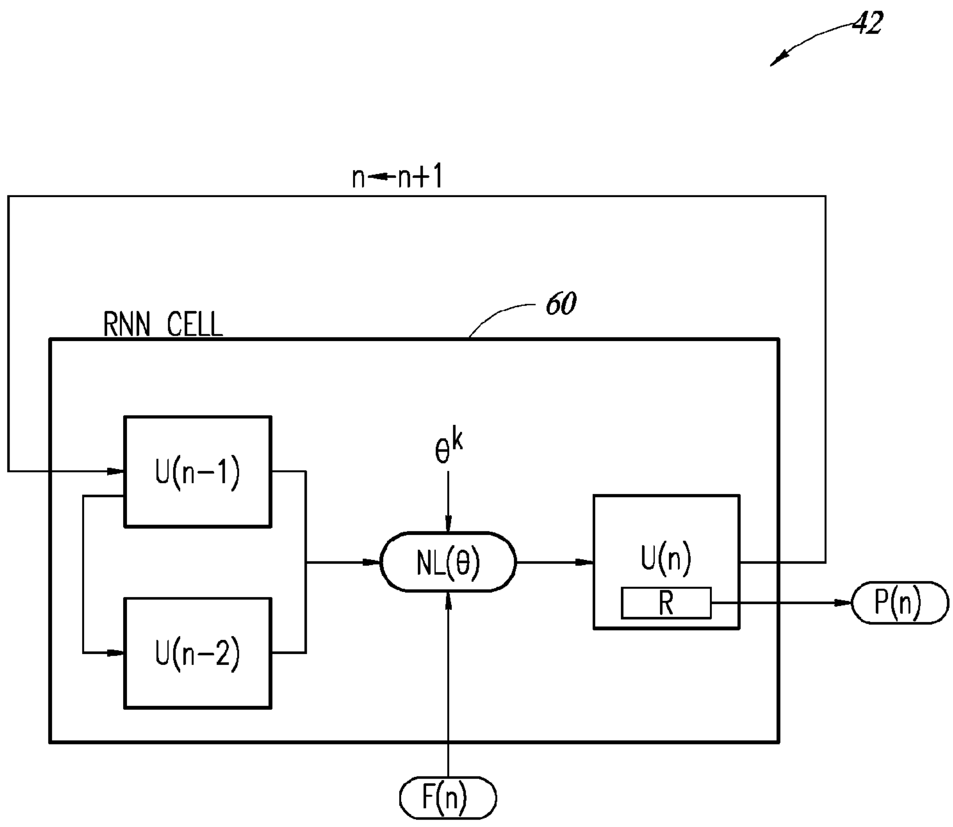
FIG. 4 is a schematic illustration of a wave field modeler, useful in the NLWIS of FIG. 2.

In accordance with a preferred embodiment of the present invention and as shown in FIG. 4 to which reference is now made, wave field modeler 42 may be implemented as an untrained neural network, where each non-linear modeler 50 and its associated restriction operator 52 may form one layer of the neural network. In particular, since the calculation for each layer is the same, the neural network may be a recurrent neural network (RNN), which is a neural network where the nodes are connected over a temporal sequence, such that the same operation is applied at each time step, allowing it to exhibit dynamic behavior. For wave field modeler 42, the time step n for the wave equation may coincide with the RNN's time step n.

FIG. 4 shows an RNN cell 60 having non-linear function NL(θ) receiving parameter estimate $\theta^k$ of the present iteration as input and to which wave samples U(n−1) and U(n−2) and pulse sample F(n) are provided. Non-linear function NL(θ) may produce current wave sample U(n) to which a restriction operator R may be applied, thereby to produce predicted sample P(n). For RNN, current wave sample U(n) may be provided to the next layer of RNN cell 60 and previous wave sample U(n−1) may be provided to the next layer of RNN cell 60 to be its U(n−2).

It will be appreciated that the goal of calculating a non-linear waveform inversion is to recover the property values in the medium and to 'discover' any other body present in the medium. However, wave field modeler 42 utilizes the unknown parameter estimate $\theta^k$ in order to calculate wave field $U^k$. At each iteration, properties adjuster 44 may adjust parameter estimate $\theta^k$ using a loss function L based on a comparison of predicted reflected waveforms P(n) with their associated measured waveforms M(n), measured by transducer 15, for each sample n. For example, loss function L may be an $L_2$ loss, between the vectorization of the predicted waveform p=vec(P) and the vectorization of the measured waveform m=vec(M), defined by equation 3:

$$L = \sum_{n=1}^{N}\left(\frac{1}{2}\|p(n) - m(n)\|_2^2\right) \tag{3}$$

Referring back to FIG. 2, properties adjuster 44 may determine the value of loss function L for iteration k using a plurality of error calculators 61 and a loss accumulator 62. Each error calculator 61 may generate an error vector $\Delta_n$=p(n)−m(n) for its sample n and loss accumulator 62 may accumulate the output of error calculators 61 as an $L_2$ loss, as per equation 3.

If loss L is acceptably small, then wave field $U^k$ may be similar to the wave field in the physical medium and properties adjuster 44 may provide property estimate $\theta^k$ to medium properties recoverer 46. Otherwise, calculated wave field $U^k$ does not represent the actual wave field in the physical medium and therefore, property estimate $\theta^k$ used in the non-linear function NL(θ) did not produce the correct model of wave field U. Accordingly, properties adjuster 44 may adjust property estimate $\theta^k$.

To this end, properties adjuster 44 may comprise a non-linear gradient calculator 64 to minimize loss L and a parameter updater 66 to update property estimate $\theta^k$ to property estimate $\theta^{k+1}$ based on the output of non-linear gradient calculator 64.

Properties adjuster 44 may perform a gradient-based operation, such as the gradient-descent, L-BFGS (limited memory Broyden-Fletcher-Goldfarb-Shanno) algorithm, Adam, or AdaDelta operations, to minimize loss L and to update property estimate $\theta^k$. Properties adjuster 44 may perform the following operation:

$$\theta^{k+1} \leftarrow \theta^k - \alpha\frac{\partial L}{\partial \Theta_k} \tag{4}$$

where α is a learning rate, set to be less than 1, and $$\frac{\partial L}{\partial \theta^k}$$

is a derivative of loss L with respect to property estimate $\theta^k$. Properties adjuster 44 may activate wave field modeler 44 for a next iteration, k+1, using the updated property estimate $\theta^{k+1}$. Wave field modeler 44 may generate new values of predicted reflected signal P(n) from the same pulse samples F(n) but with the updated parameter vector $\theta^{k+1}$.

To calculate equation 4, non-linear gradient calculator 64 may determine derivative $$\frac{\partial L}{\partial \theta^k}.$$

In accordance with a preferred embodiment of the present invention, non-linear gradient calculator 64 may be implemented via the backpropagation portion of a neural network system, which performs differentiation on the function implemented by the neural network.

Figure 5:
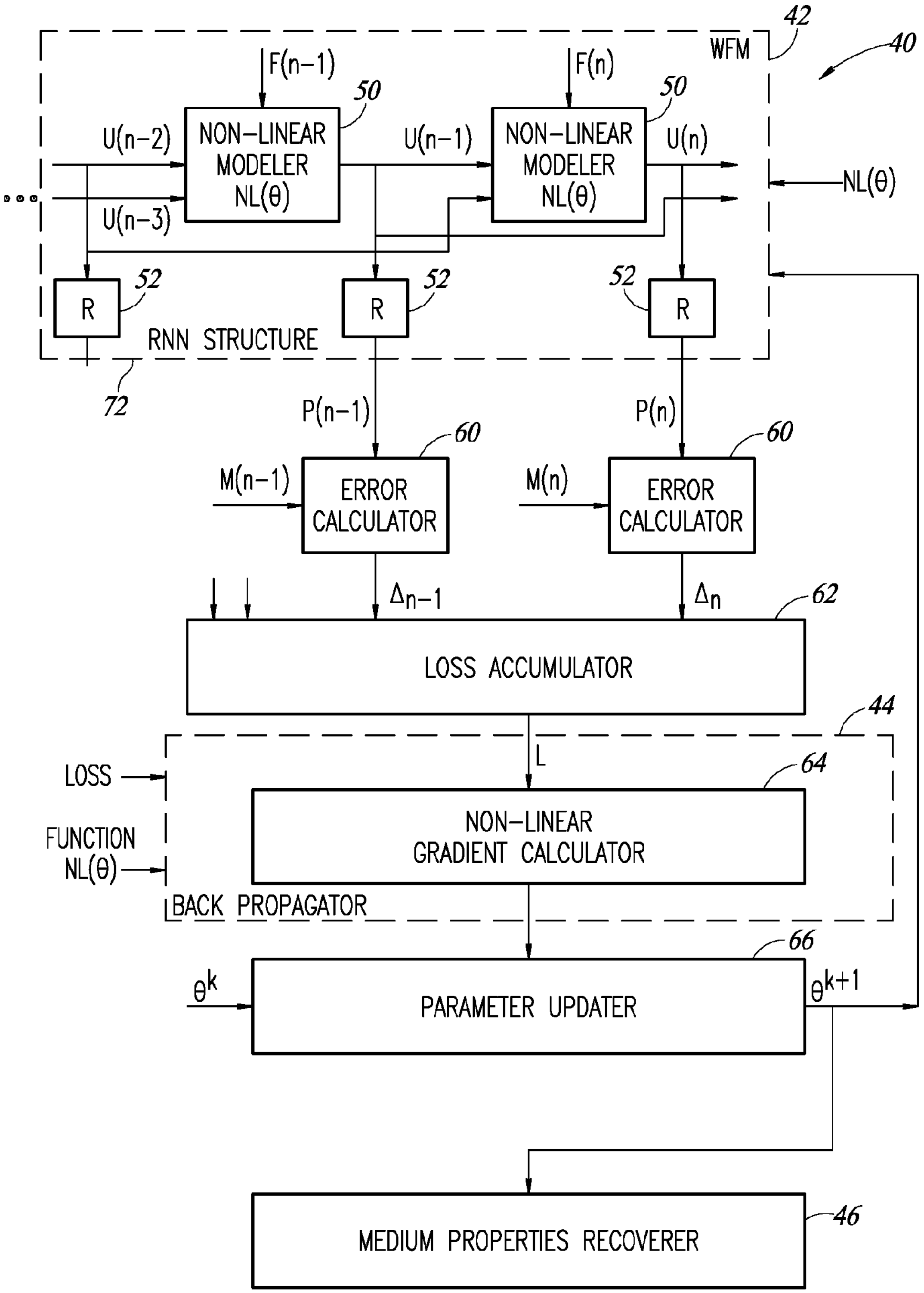
FIG. 5 is a schematic illustration of an implementation of the NLWIS system of FIG. 2 using neural network tools.
Figure 6A:
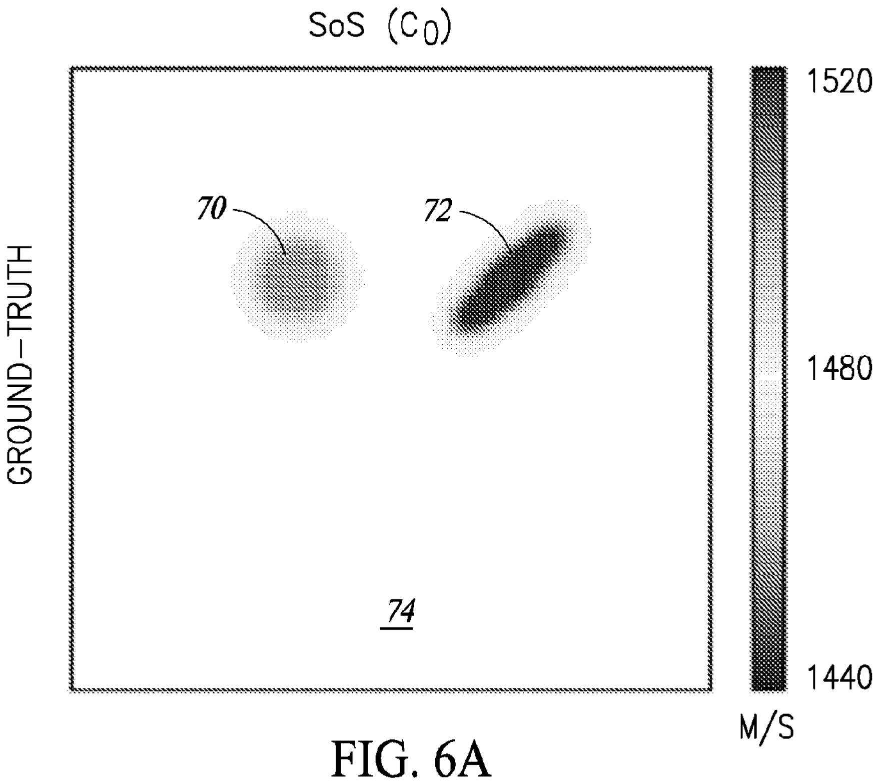
FIGS. 6A, 6B, 6C and 6D are graphical representations of ground truth values for four properties, respectively.
Figure 6B:
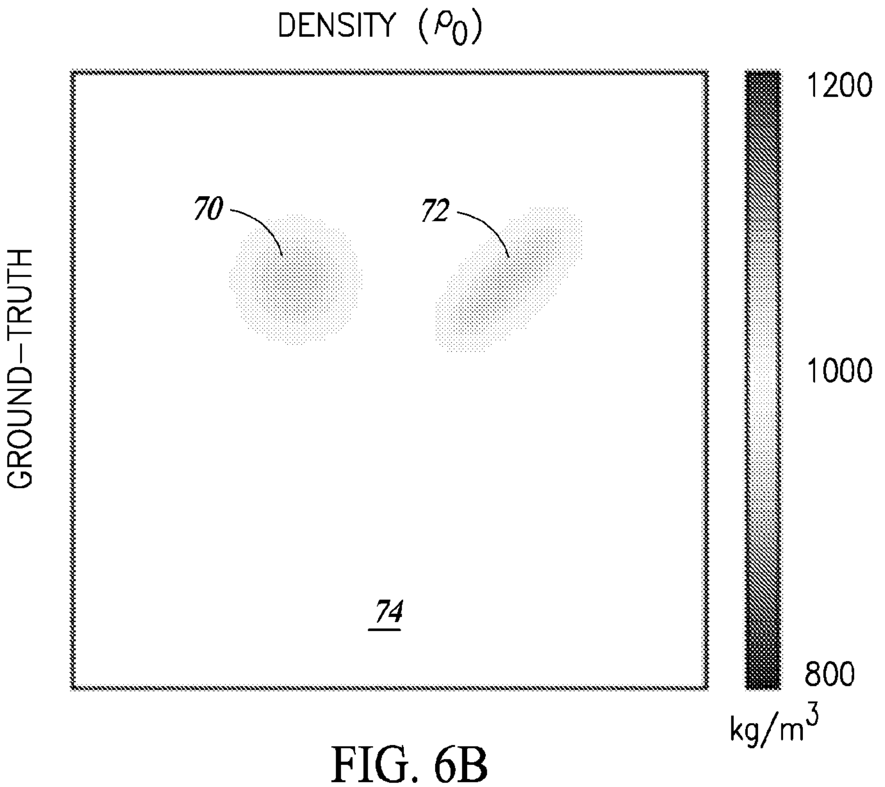
Figure 6C:
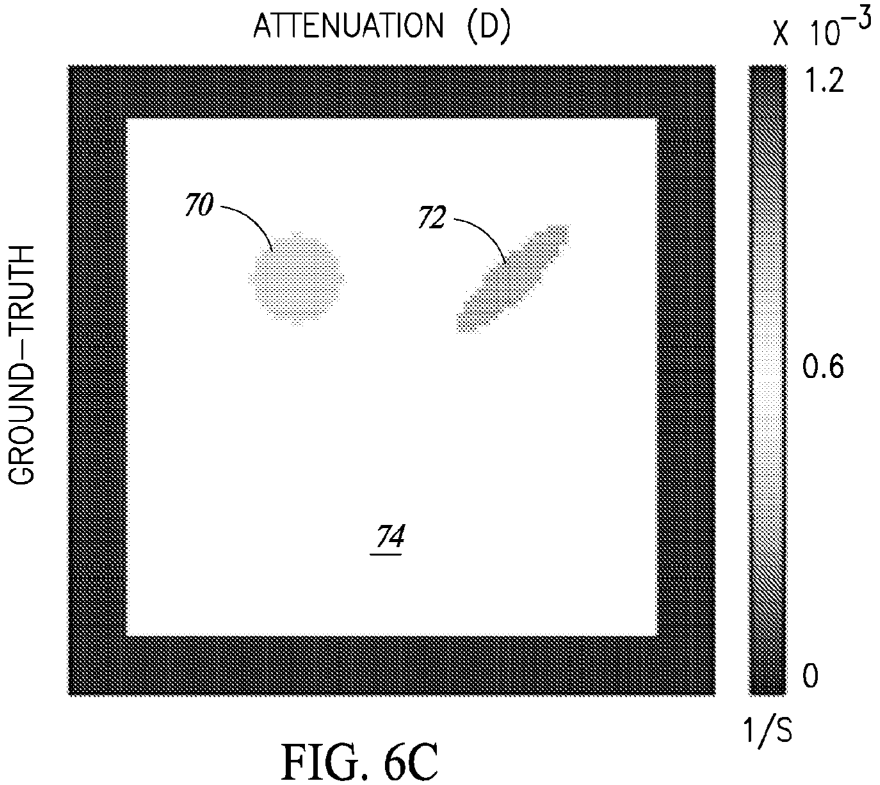
Figure 6D:
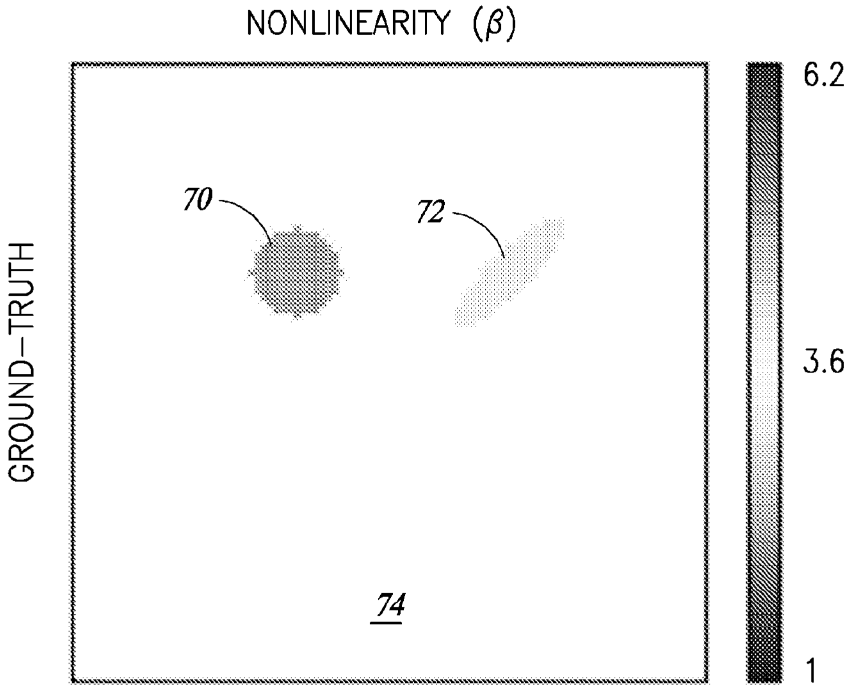
Figure 6E:
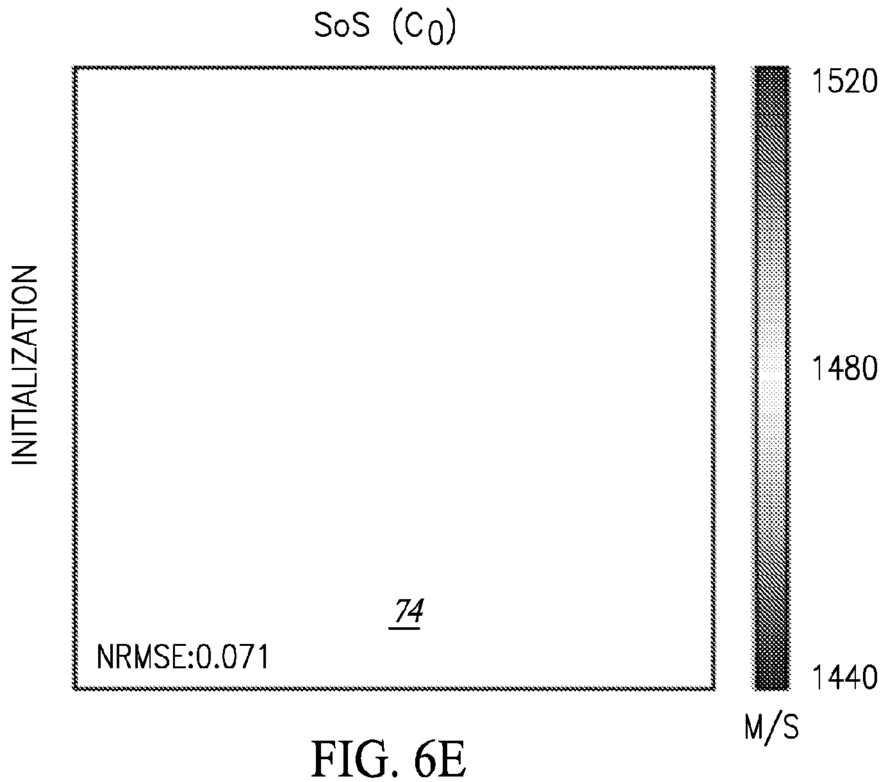
FIGS. 6E, 6F, 6G and 6H are graphical representations of initial values used as input to the NLWSI system of FIG. 2 for the properties of FIGS. 6A, 6B, 6C and 6D, respectively.
Figure 6F:
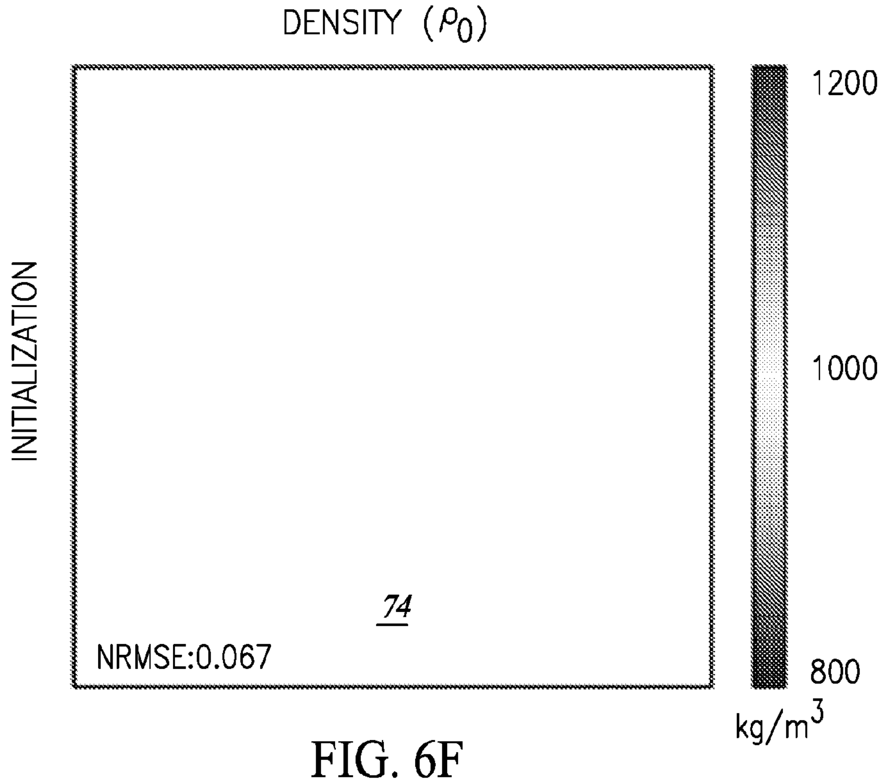
Figure 6G:
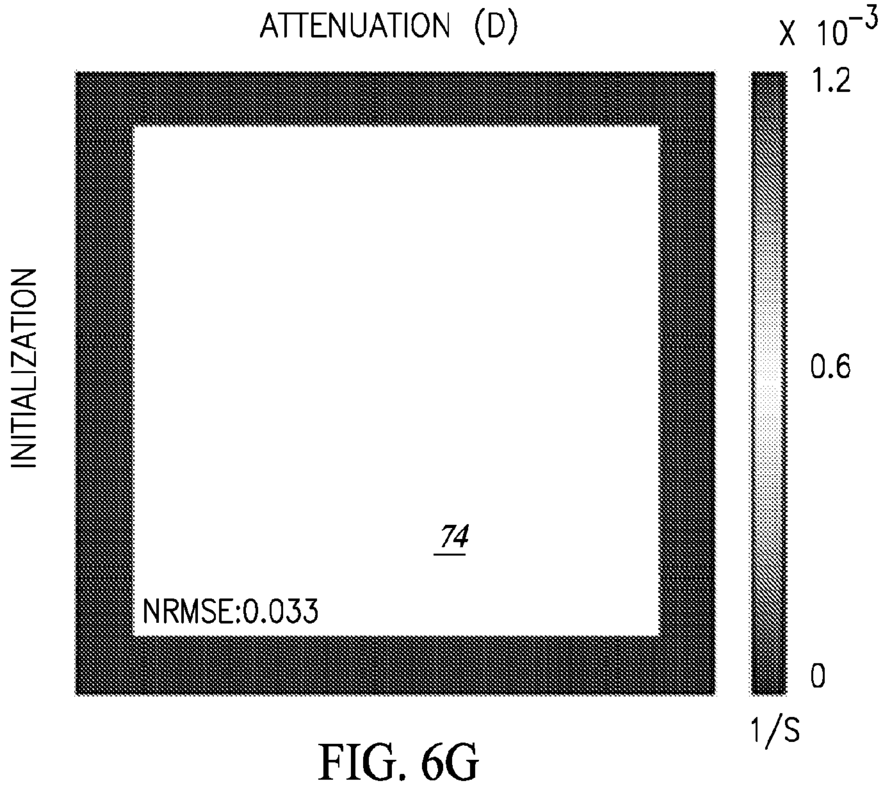
Figure 6H:
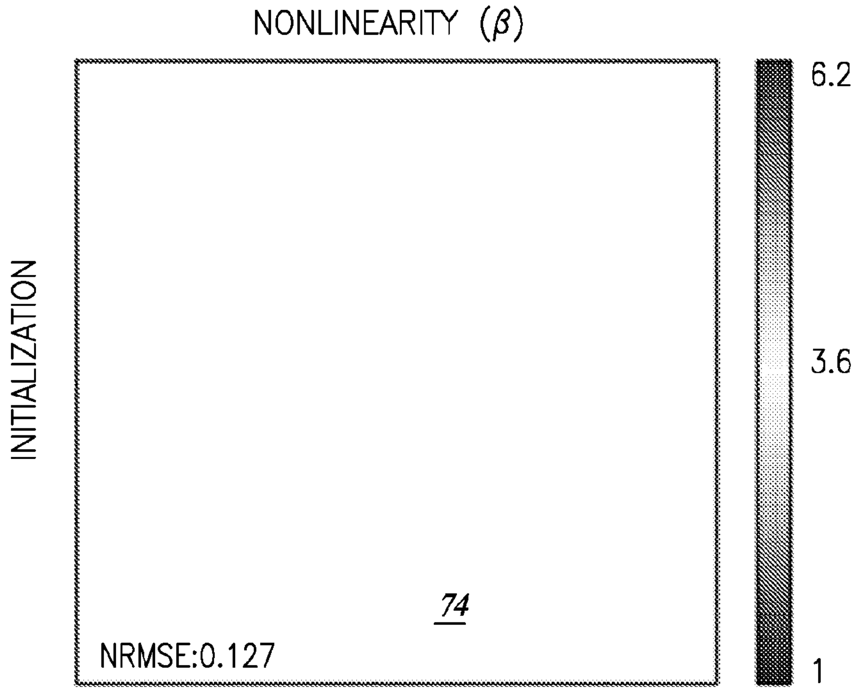
Figure 6I:
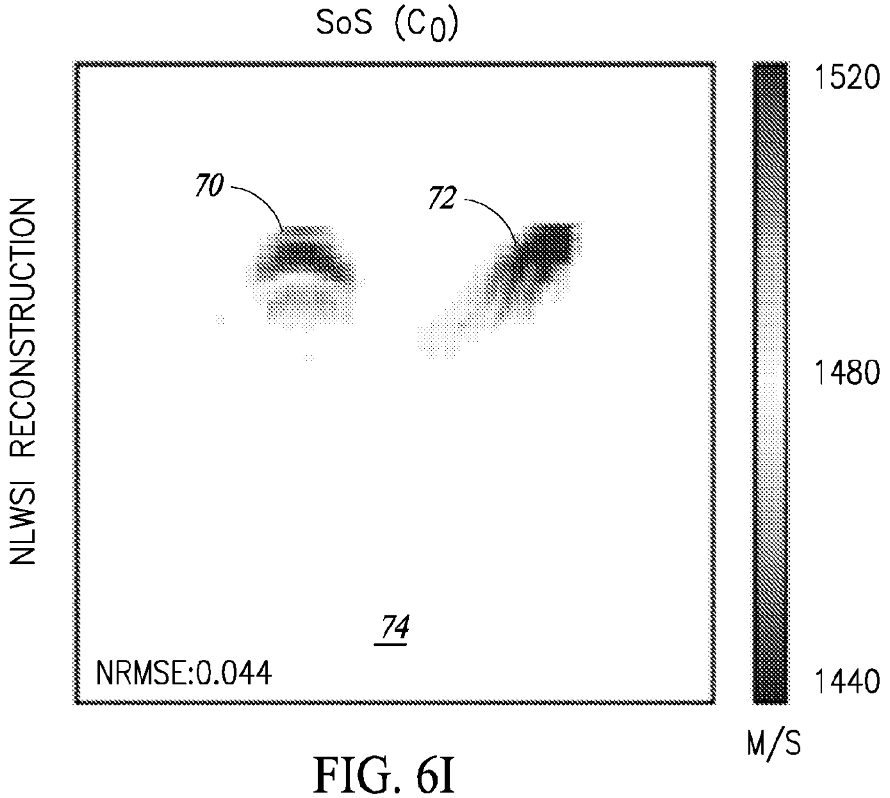
FIGS. 6I, 6J, 6K and 6L are graphical representations of the reconstructions produced by the NLWSI system of FIG. 2 for the properties of FIGS. 6A, 6B, 6C and 6D, respectively.
Figure 6J:
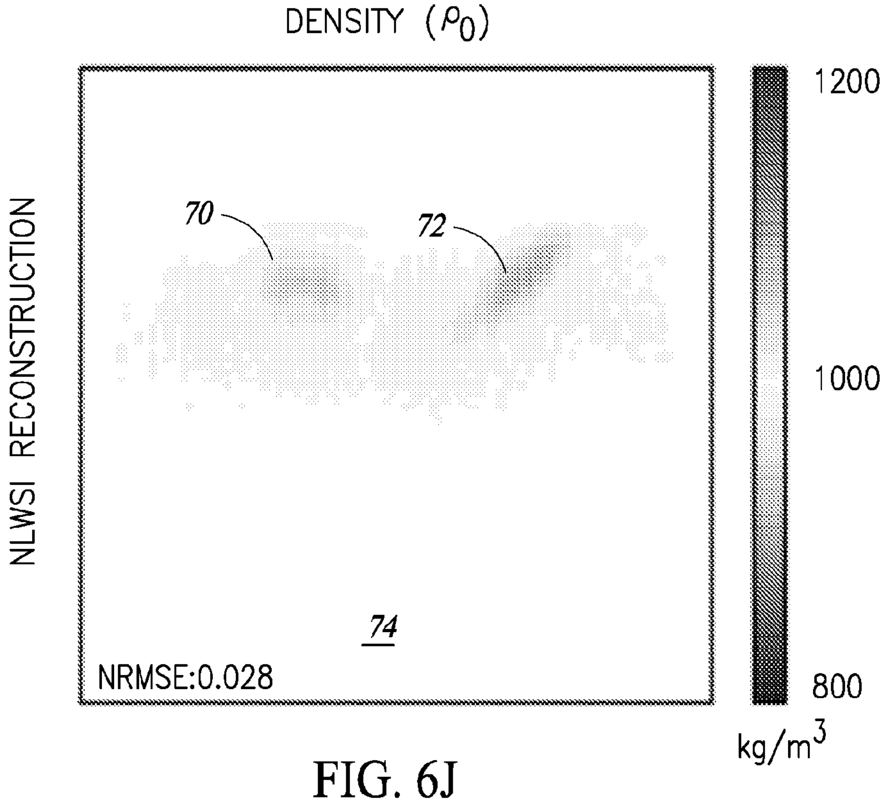
Figure 6K:
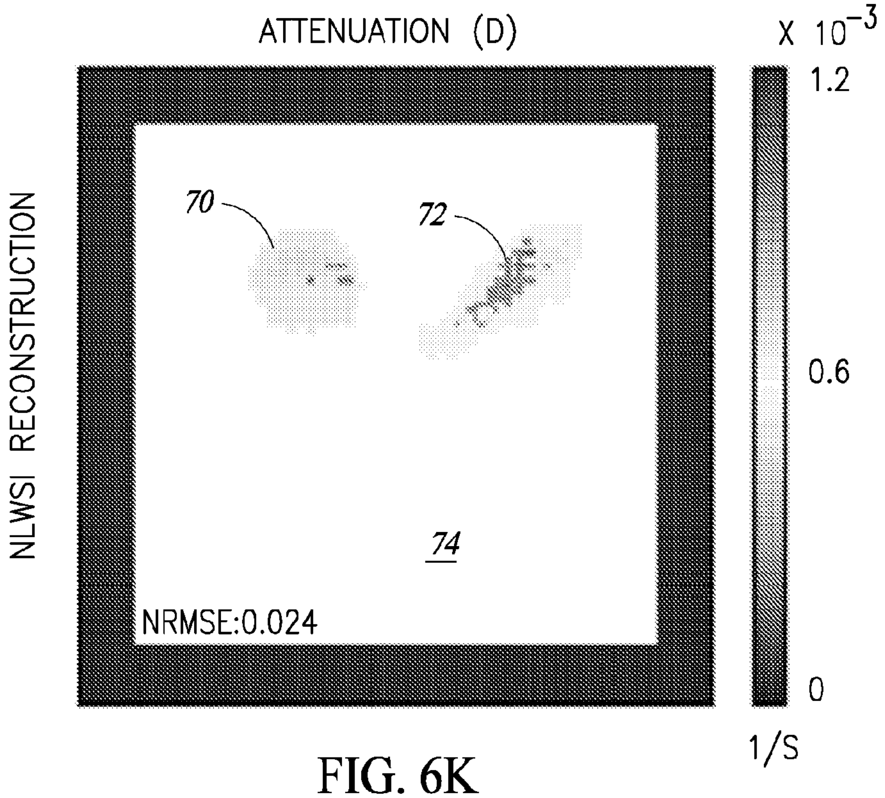
Figure 6L:
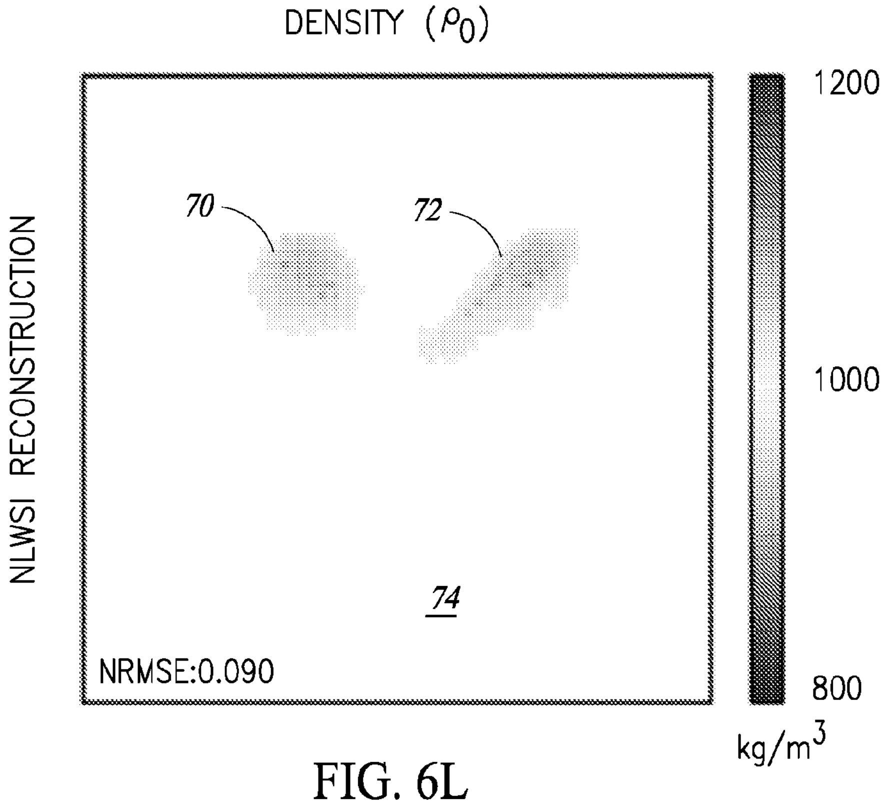

Reference is now made to FIG. 5, which illustrates the implementation of system 40 using neural network tools. As can be seen, wave field modeler 42 may be implemented or modeled using a neural network structure and specifically, a recurrent neural network (RNN) structure 72 built using non-linear function NL(θ) as its recurrence relation. Non-linear gradient calculator 64 may be implemented as a backpropagator which may exploit the recurrence relation NL(θ) to backpropagate the gradients through RNN 72, returning the gradients of wave field $U^k$ with respect to the physical properties $$\left(\text{i.e., } \frac{\partial U}{\partial \theta^k}\right).$$

From these gradients, parameter updater 66, which may compute the derivative of the loss function of equation 4, may compute, $$\frac{\partial P}{\partial \theta^k},$$

and from that, may compute $$\frac{\partial L}{\partial \theta^k},$$

as provided in equation 5:

$$\frac{\partial L}{\partial \theta^k} = \left(\frac{\partial p}{\partial \theta^k}\right)^T (p - m) \quad (5)$$

Applicant has realized that, by using the backpropagation system of an RNN network, the gradients of any wave equation may be computed when represented in the discrete representation of equation 1.

It will be appreciated that, in the prior art, the back propagation tools in a neural network platform were used for the training of a neural network. System 40 does not use the neural network tools for learning and training a neural network. Instead, system 40 uses an RNN to express its objective function (i.e. the calculation of wave field U) and then exploits the expression as an RNN to facilitate computation of the gradients for the optimization process. As a result, the gradient computation may utilize the advanced optimization algorithms (i.e. the various backpropagation algorithms) used for neural networks and other deep-learning systems.

In an alternative embodiment, the wave field modeler can be implemented with a neural network structure without recurrence, such as a deep neural network, where the layers express the time-dependence of the equation, similar to the structure shown in FIG. 2. In this embodiment, the relation between the consecutive layers is determined by the recurrence relation NL(θ). For neural networks without recurrence, the layers of a deep neural network coincide with the RNN's time step n.

It will further be appreciated that although the present invention focuses on ultrasound imaging, and its non-linear wave equation, the NLWSI system may operate on other types of physical waves. Thus, it may be implemented to determine wave fields which can be acoustic, electromagnetic, elastic, photoacoustic, or acousto-optic waves.

It will also be appreciated that, similar to the linear FWI algorithm and contrary to geometry-based methods for nonlinear property recovery, system 40 may be activated with an arbitrary type of pulse F, for example, a plane wave, a diverging wave, or a focused beam. The system may also be implemented utilizing any transducer array geometry, captured by the restriction operator, such as linear, convex, elliptic and endo-cavitary probes.

Applicant has realized that, compared to a linear waveform inversion, an increased amount of information may be extracted from a non-linear waveform inversion, including additional physical properties (such as the medium's nonlinearity). An improved contrast and resolution of the reconstructed properties can be obtained.

In an exemplary implementation, the results of which are shown in FIGS. 6A-6L to which reference is now made, the properties of a 50 mm×50 mm simulated medium with similar characteristics to those of human tissues were reconstructed from ultrasound signals. The transducer array was a linear transducer array of 80 ultrasound elements which issued acoustic pulses, F(n), generated by 16 transducer elements, with a central frequency of $f_0$=4 MHz. The pulses were focused beams, with a focus depth of 5 mm and with no steering angle, as discussed in more detail hereinbelow. The transducer performed 16 consecutive lateral insonifications of the focused beam, moving along the array.

Noise signals were added to the simulated signal. These additive noises were normally distributed with zero means. The variance was chosen such that the obtained signal-to-noise ratio (SNR) was 20, imitating in-vivo US scans.

In this example, the loss was a regularized $L_2$ loss:

$$L(\{\theta_i\}_{i=1}^{m}, m) = \left\|P(\{\theta_i\}_{i=1}^{n_\theta}, F) - M\right\|_F + \sum_{i=1}^{n_\theta=4} \lambda_{\theta_i} \|D_S \theta_i\|_F \quad (6)$$

where $n_\theta$ is the number of parameters, $P \in \mathbb{R}^{n_c \times n_t}$ is the predicted signal, and $M \in \mathbb{R}^{n_c \times n_t}$ is the measured signal, where $n_t$ is the number of time samples. In addition, $D_S$ is the Sobel regularization operator that enforces soft edges, and $\lambda_{\theta_i} \in R$ for $i \in |1, n_\theta|$ controls the level of regularization. At each iteration, the estimates were updated using the Adam optimizer.

In FIGS. 6A-6L, the simulated medium contained two types of tissues placed in water 74, where the left tissue 70 is of fat and the right tissue 72 is of liver. FIGS. 6A, 6B, 6C and 6D provide the ground truth values for the four properties—SoS, density, attenuation and nonlinearity, respectively. FIGS. 6E, 6F, 6G and 6H show the initial values used as input to the inverse algorithm and FIGS. 6I, 6J, 6K and 6L, respectively, show the reconstructions using system 40.

To initialize system 40 (i.e. at iteration k=0), the medium was assumed to contain mostly water, and therefore, the properties estimate $\theta^0$ was initialized with values corresponding to water (e.g., the SoS map was initialized to the SoS of water (i.e. 1480 m/s) and the density map is initialized to the density of water (i.e. 1000 kg/m$^3$)).

An NRMSE (normalized root mean squared error) evaluation metric was used to evaluate how close each iteration came to the ground truth values $\theta^{GT}$ of the parameters, providing a value in the range of [0,1], as follows:

$$NRMSE(\theta^k) = \frac{\sqrt{\|\theta^k - \theta^{GT}\|_F^2 / (n_x n_z)}}{\theta^{GTmax} - \theta^{GTmin}} \quad (7)$$

where $\theta^k$ are the reconstructed properties at iteration k, and $\theta^{GTmax}$ and $\theta^{GTmin}$ are predefined upper and lower and bounds on the estimated property values, respectively.

In the example of FIGS. 6A-6L, the estimates of the SoS and density parameters were completed first, before the attenuation and nonlinearity parameters. As a result, the previously reconstructed density values were used to create a mask indicating the tissues' locations inside the medium and the mask was used in the estimation of the attenuation and nonlinearity parameters. To generate the density map, the density values were reviewed to find those regions in the reconstructed density map with values that are distant from the density of the water by a predefined threshold. The estimations of the damping and the nonlinearity parameter were then updated only in a restricted region of the medium, defined by the mask.

As can be seen from FIG. 6A-6L, system 40 successfully reconstructed tissues 70 and 72 for each parameter, including the nonlinearity parameter.

It will be appreciated that embodiment provided above is exemplary and that the variables may be 2- or 3-dimensional matrices of any size, as appropriate to the waveform being inverted.

Unless specifically stated otherwise, as apparent from the preceding discussions, it is appreciated that, throughout the specification, discussions utilizing terms such as "processing," "computing," "calculating," "determining," or the like, refer to the action and/or processes of a general purpose computer of any type, such as a client/server system, mobile computing devices, smart appliances, cloud computing units or similar electronic computing devices that manipulate and/or transform data within the computing system's registers and/or memories into other data within the computing system's memories, registers or other such information storage, transmission or display devices.

Embodiments of the present invention may include apparatus for performing the operations herein. This apparatus may be specially constructed for the desired purposes, or it may comprise a computing device or system typically having at least one processor and at least one memory, selectively activated or reconfigured by a computer program stored in the computer. The resultant apparatus when instructed by software may turn the general purpose computer into inventive elements as discussed herein. The instructions may define the inventive device in operation with the computer platform for which it is desired. Such a computer program may be stored in a computer readable storage medium, such as, but not limited to, any type of disk, including optical disks, magnetic-optical disks, read-only memories (ROMs), volatile and non-volatile memories, random access memories (RAMs), electrically programmable read-only memories (EPROMs), electrically erasable and programmable read only memories (EEPROMs), magnetic or optical cards, Flash memory, disk-on-key or any other type of media suitable for storing electronic instructions and capable of being coupled to a computer system bus. The computer readable storage medium may also be implemented in cloud storage.

Some general purpose computers may comprise at least one communication element to enable communication with a data network and/or a mobile communications network.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the invention as described herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A system for recovering physical properties from a non-linear medium, the system comprising:

a wave field modeler to model a wave field generated by at least one transmitted pulse as it travels in said non-linear medium and to generate a predicted transducer output from said modeled wave field, said wave field modeler being implemented as a recurrent neural network (RNN) wherein each layer of the RNN corresponds to a discrete time step of the wave propagation and implements a discrete version of a physics-based non-linear wave equation using an initial set of physical properties of the medium-;

a properties adjuster to iteratively update the set of physical properties by:

receiving a loss function value representing a difference between the predicted transducer output and a measured transducer output; and operating a backpropagator through said RNN to adjust the set of physical properties to minimize the loss function, thereby generating an improved set of said physical properties for a subsequent iteration of said wave field modeler; and a medium properties recoverer to output a final improved set of said physical properties once said properties adjuster reaches a convergence criterion, wherein said final set of physical properties constitutes said recovered physical properties of said non-linear medium.

2. The system according to claim 1 wherein said non-linear medium is a two or three dimensional body tissue.

3. The system according to claim 1 wherein said wave field is one of: an acoustic, an electromagnetic, an elastic, a photo-acoustic, and an acousto-optic wave.

4. The system according to claim 1 wherein said at least one transmitted pulse is one of: a plane wave, a focused beam, and a diverging wave.

5. The system according to claim 1 wherein said RNN comprises a non-linear function receiving said improved set of said physical parameters as input and to which two previous wave samples and a pulse sample are provided.

6. The system according to claim 5 wherein said wave field modeler also comprises a restriction operator to restrict said predicted transducer output of said RNN to one of a linear array of elements, a convex array of elements, an elliptic array of elements, and an endo-cavitary array of elements.

7. The system according to claim 1 wherein said properties adjuster comprises:

a plurality of error calculators, wherein each error calculator of said plurality of error calculators is associated with a wave field sample and each error calculator generates an error vector between said predicted transducer output and said measured transducer output for its associated wave field sample;

a loss accumulator to accumulate said plurality of error vectors; and a non-linear gradient calculator, implemented by said backpropagator, to exploit said non-linear wave function to backpropagate gradients through said neural network, thereby to return gradients of said wave field with respect to said set of physical properties.

8. A method for recovering physical properties from a non-linear medium, the method comprising:

modeling a wave field generated by at least one transmitted pulse as it travels in said non-linear medium, said modeling using a recurrent neural network (RNN) wherein each layer of the RNN corresponds to a discrete time step of the wave propagation and implements a discrete version of a physics-based non-linear wave equation using an initial set of physical properties of the medium;

generating a predicted transducer output from said modeled wave field;

iteratively updating the set of physical properties by:

receiving a loss function value representing a difference between the predicted transducer output and a measured transducer output; and operating a backpropagator through the RNN to adjust the set of physical properties to minimize the loss function, thereby generating an improved set of said physical properties for a subsequent iteration of the wave field modeler;

activating said modeling with said improved set of said physical properties; and providing a final improved set of said physical properties once said optimizing reaches a convergence criterion, wherein said final set of physical properties constitutes said recovered physical properties of said non-linear medium.

9. The method according to claim 8 wherein said non-linear medium is a two or three dimensional body tissue.

10. The method according to claim 8 wherein said wave field is one of: an acoustic, an electromagnetic, an elastic, a photo-acoustic, and an acousto-optic wave.

11. The method according to claim 8 wherein said at least one transmitted pulse is one of: a plane wave, a focused beam, and a diverging wave.

12. The method according to claim 8 wherein said RNN comprises a non-linear function receiving said improved set of said physical parameters as input and to which two previous wave samples and a pulse sample are provided.

13. The method according to claim 12 wherein said modeling also comprises restricting said predicted transducer output of said RNN to one of a linear array of elements, a convex array of elements, an elliptic array of elements, and an endo-cavitary array of elements.

14. The method according to claim 8 wherein said iteratively updating comprises:

generating a plurality of error vectors, each error vector being associated with a wave field sample, each said error vector defining a difference between said predicted transducer output and said measured transducer output for its associated wave field sample;

accumulating said plurality of error vectors; and exploiting said non-linear wave function to backpropagate gradients through said neural network, thereby to return gradients of said wave field with respect to said set of physical properties.

* * * * *